US011932255B2

(12) United States Patent
Neagu Chivu et al.

(10) Patent No.: US 11,932,255 B2
(45) Date of Patent: Mar. 19, 2024

(54) METHOD OF PROCESSING THE PSYCHOPHYSICAL STATE OF A DRIVER TO IMPROVE THE DRIVING EXPERIENCE OF A ROAD VEHICLE AND RELATED VEHICULAR SYSTEM

(71) Applicant: FERRARI S.p.A., Modena (IT)

(72) Inventors: Mihaela Neagu Chivu, Modena (IT); Andrea Secondi, Modena (IT)

(73) Assignee: FERRARI S.p.A., Modena (IT)

( * ) Notice: Subject to any disclaimer, the term of this patent is extended or adjusted under 35 U.S.C. 154(b) by 0 days.

(21) Appl. No.: 17/840,493

(22) Filed: Jun. 14, 2022

(65) Prior Publication Data
US 2022/0402502 A1 Dec. 22, 2022

(30) Foreign Application Priority Data

Jun. 16, 2021 (IT) .......................... 102021000015695

(51) Int. Cl.
*B60W 40/08* (2012.01)
*A61B 5/00* (2006.01)
(Continued)

(52) U.S. Cl.
CPC ......... *B60W 40/08* (2013.01); *A61B 5/02055* (2013.01); *A61B 5/024* (2013.01);
(Continued)

(58) Field of Classification Search
CPC .. B60W 40/08; B60W 50/0098; B60W 50/14; B60W 2040/0872; B60W 2420/42;
(Continued)

(56) References Cited

U.S. PATENT DOCUMENTS 11,667,195 B2 * 6/2023 Luken ...................... G09G 5/37
701/99
2011/0213511 A1 9/2011 Visconti et al.
(Continued)

FOREIGN PATENT DOCUMENTS

DE 102016215250 A1 2/2018
EP 3158392 B1 4/2020
(Continued)

OTHER PUBLICATIONS

Search Report for Italian Application No. 102021000015695, completed Mar. 21, 2022, 9 pages.
(Continued)

*Primary Examiner* — Ryan W Sherwin
(74) *Attorney, Agent, or Firm* — CANTOR COLBURN LLP

(57) ABSTRACT

A method of processing the psychophysical state of a driver to improve the driving experience of road vehicle driven by a driver and comprising the steps of: cyclically detecting one or more objective vital parameters of the driver by means of one or more first sensors installed within a vehicular system; processing the value of a vital state index according to said one or more objective vital parameters detected; cyclically detecting one or more subjective parameters of the driver by means of one or more second sensors installed within the vehicular system; processing, starting from the objective vital parameters and according to the subjective parameters, the psychophysical state of the driver.

14 Claims, 5 Drawing Sheets

(51) Int. Cl.
*A61B 5/0205* (2006.01)
*A61B 5/024* (2006.01)
*A61B 5/18* (2006.01)
*A61B 5/318* (2021.01)
*B60W 50/00* (2006.01)
*B60W 50/14* (2020.01)
*G06V 20/59* (2022.01)
*G06V 40/16* (2022.01)
*G10L 25/66* (2013.01)

(52) U.S. Cl.
CPC .............. *A61B 5/18* (2013.01); *A61B 5/318* (2021.01); *A61B 5/6802* (2013.01); *B60W 50/0098* (2013.01); *B60W 50/14* (2013.01); *G06V 20/597* (2022.01); *G06V 40/174* (2022.01); *G10L 25/66* (2013.01); *B60W 2040/0872* (2013.01); *B60W 2420/42* (2013.01); *B60W 2420/54* (2013.01); *B60W 2540/22* (2013.01); *B60W 2540/221* (2020.02)

(58) Field of Classification Search
CPC ......... B60W 2420/54; B60W 2540/22; B60W 2540/221; B60W 2300/28; B60W 2040/0818; B60W 2422/00; B60W 2540/21; B60W 2540/215; B60W 2540/26; B60W 2040/0827; A61B 5/02055; A61B 5/024; A61B 5/18; A61B 5/318; A61B 5/6802; A61B 5/6893; A61B 5/6803; A61B 5/6804; A61B 5/6806; G06V 20/597; G06V 40/174; G10L 25/66; B60Y 2200/114; B60K 28/06

See application file for complete search history.

(56) References Cited

U.S. PATENT DOCUMENTS

| | | | |
|---|---|---|---|
| 2014/0152792 A1* | 6/2014 | Krueger | A61B 5/4863 348/78 |
| 2017/0129397 A1* | 5/2017 | Gee | B60Q 5/008 |
| 2018/0022358 A1* | 1/2018 | Fung | G06V 40/70 701/36 |
| 2019/0061772 A1 | 2/2019 | Prinz | |
| 2019/0375426 A1* | 12/2019 | Suga | B60W 50/08 |
| 2020/0114925 A1* | 4/2020 | Iwasaki | G06V 40/174 |

FOREIGN PATENT DOCUMENTS

| | | | | |
|---|---|---|---|---|
| WO | 2015/138515 A1 | 9/2015 | | |
| WO | WO-2016116849 A1 * | 7/2016 | ............... | B62D 1/04 |

OTHER PUBLICATIONS

Katsis, Christos D. et al., "Toward Emotion Recognition in Car-Racing Drivers: A Biosignal Processing Approach," IEEE Transactions on Systems, Man, and Cybernetics—Part A: Systems and Humans, vol. 38, No. 3., May 2008, pp. 502-512.

* cited by examiner

METHOD OF PROCESSING THE PSYCHOPHYSICAL STATE OF A DRIVER TO IMPROVE THE DRIVING EXPERIENCE OF A ROAD VEHICLE AND RELATED VEHICULAR SYSTEM

CROSS-REFERENCE TO RELATED APPLICATIONS

This patent application claims priority from Italian patent application no. 102021000015695 filed on Jun. 16, 2021, the entire disclosure of which is incorporated herein by reference.

TECHNICAL SECTOR

The invention relates to a method of processing the psychophysical state of a driver to improve the driving experience of a road vehicle and to a related vehicular system. In particular, the invention finds advantageous, though non-exclusive application in a high-performance road vehicle, more in particular while driving on a track, to which explicit reference will be made in the description below without because of this losing in generality.

PRIOR ART

Generally speaking, different functions of a road vehicle, especially of a high-performance road vehicle, can be adjusted based on the behaviour of the vehicle itself (dynamic parameters), on its conditions (wear) and on how a driver interacts with it (driving style).

As a matter of fact, nowadays, the driving experience and the training of drivers/pilots are improved through a common standard, which exclusively uses, as feedback, vehicle parameters aimed at reaching a common sensation of well-being or an objective management of track performances.

However, the state of the art dealing with the improvement of the driving experience does not take into account the subjectivity of each single driver, who perceives the driving experience and the performance-related sensations in a unique manner, differently from other drivers.

Recently, systems were developed, which are designed to analyse the psychophysical state of a driver when he/she enters the vehicle and/or is driving, in particular to check for a possible state of drunkenness (through blood alcohol content test) and, if necessary, to prevent the vehicle from turning on or to monitor the tiredness of the driver and to suggest a break. In the last case, these systems are usually provided with optical sensors, for example cameras, to assess, for instance, the opening of the eyelids of the driver.

However, these system are exclusively focused on the safety on roads open to traffic and are not in any way aimed at improving the driving experience of the driver. Furthermore, these systems are limited to a generally visual assessment of the driver and currently do not take into account the subjectivity of different drivers; for example, a driver can be tired even without changing the opening of the eyelid, just like a driver can be perfectly concentrated even if he/she partially closes the eyelids.

DESCRIPTION OF THE INVENTION

The object of the invention is to provide a method of processing the psychophysical state of a driver to improve the driving experience of a road vehicle and a related vehicular system, which are at least partially free from the drawbacks described above and, at the same time, are simple and economic to be carried out and manufactured.

According to the invention, there are provided a method of processing the psychophysical state of a driver to improve the driving experience of a road vehicle and a related vehicular system as claimed in the appended claims.

The appended claims describe preferred embodiments of the invention and form an integral part of the description.

BRIEF DESCRIPTION OF THE DRAWINGS

The invention will now be described with reference to the accompanying drawings, which show some non-limiting embodiments thereof, wherein.

PREFERRED EMBODIMENTS OF THE INVENTION

Figure 1:
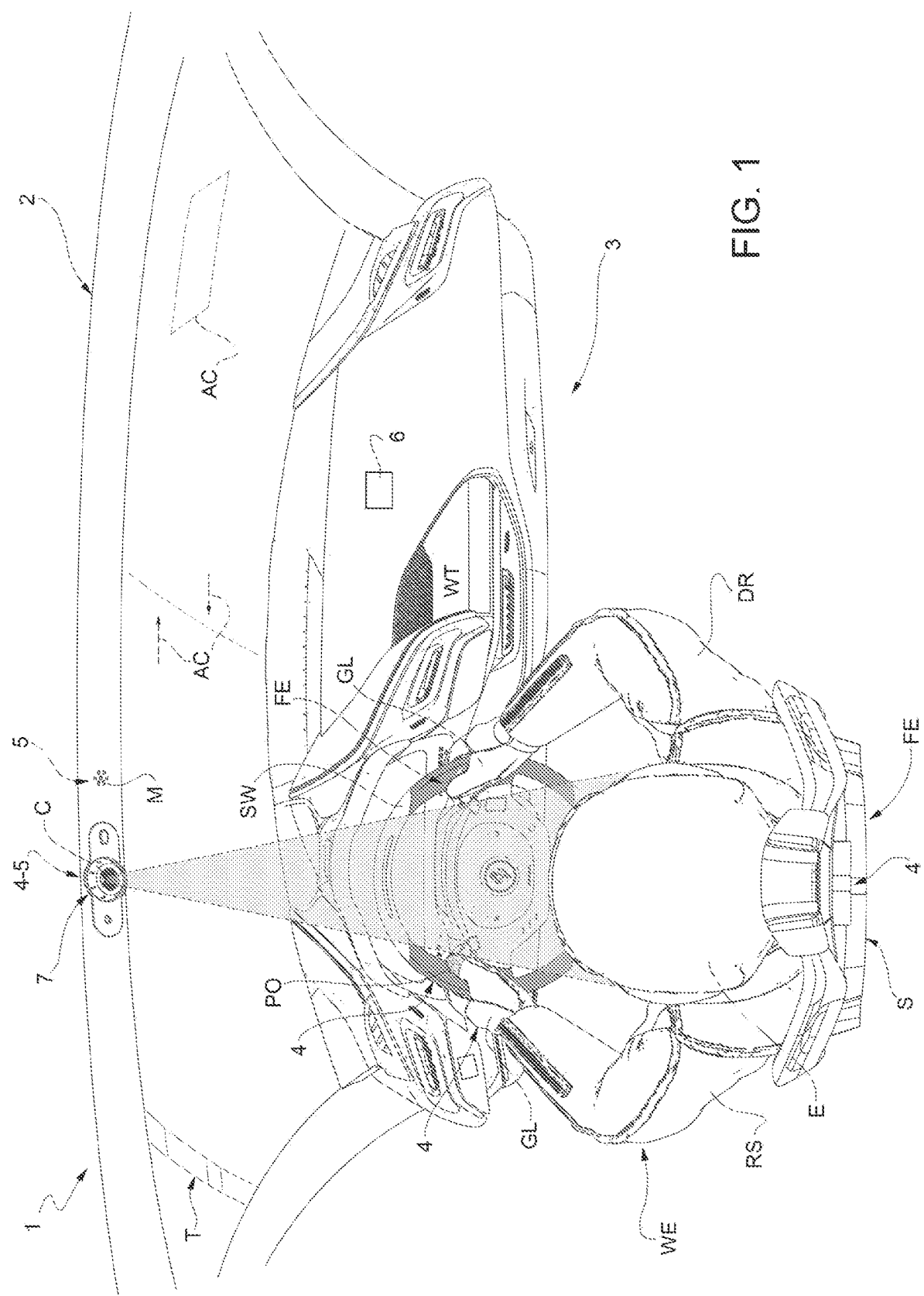
FIG. 1 is a first schematic perspective view, in particular rear view, of a portion of a vehicular system according to the invention.

In FIG. 1, number 1 indicates, as a whole, a vehicular system to improve the driving experience of a road vehicle 2 driven by a driver DR and provided with two front wheels W and with two rear wheels (in particular, drive wheels). The vehicle 2 is provided with a passenger compartment 3, which is designed to accommodate the driver DR and possible passengers. The term "driving experience" encompasses both experiences relating to the comfort inside the vehicle and experiences concerning the management of the vehicle in terms of performances, namely on a track. In the last case, an experience turns out to be improved if it improves performances or, anyway, provides the driver with a greater awareness of his/her performances.

In particular, the vehicular system 1 is configured to process the psychophysical state of the driver DR so as to improve his/her driving experience, more precisely his/her performances on a track T (namely the lap time). The term "psychophysical state" indicates all those states concerning the emotion/sensation or the set of emotions/sensations felt by the driver DR. For example, psychophysical states are: stress, anxiety, sadness, tiredness, indifference (neutral state), happiness, joy, surprise, fear . . . .

Figure 5:
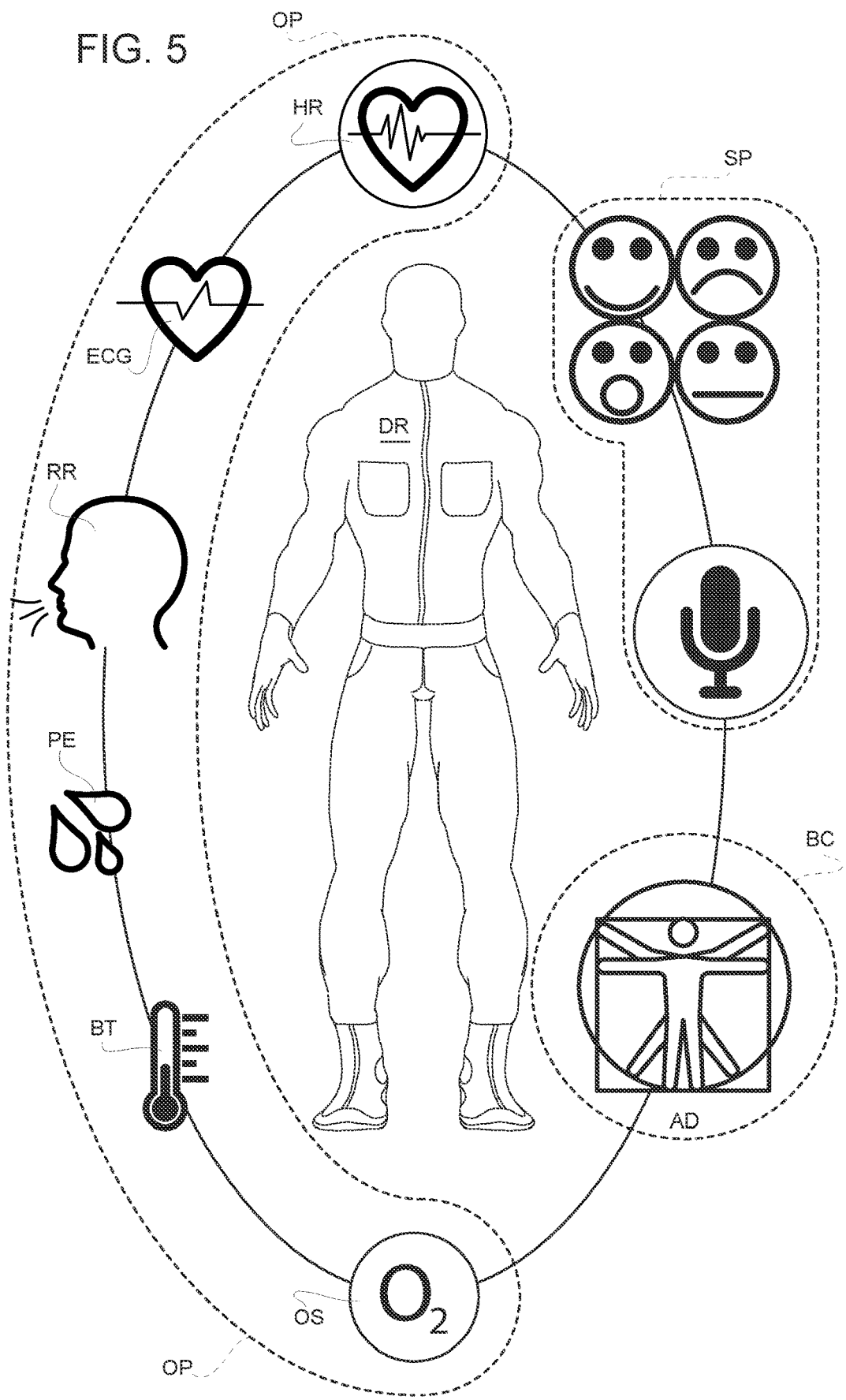
FIG. 5 is a schematic view of a plurality of objective vital parameters, subjective parameters and boundary conditions used in the diagram of FIG. 1.

The vehicular system 1 comprises (in particular, besides the vehicle 2) one or more sensor devices 4 configured to detect, in use, one or more objective vital parameters OP of the river DR (see, for example, FIG. 5). The objective vital parameters OP of the driver DR are all those parameters that can be measured by means of suitable systems and relate to physical/chemical conditions of the body of the driver DR capable of providing useful indications on his/her state. These parameters are considered objective for they have, for each person, normal values and abnormal values (higher or lower than normal values).

Advantageously, though not necessarily, the vital parameters OP comprise heart rate HR and/or electrocardiogram ECG and/or respiratory rate RR and/or body temperature BT and/or oxygen saturation OS. Alternatively or in addition, the objective vital parameters OP comprise: arterial pressure and/or oxygen consumption and/or energy expenditure (for example, by means of a metabolimeter) and/or electrodermal activity (EDA) and/or sweat gland activity PE. In some non-limiting cases, the vital parameters OP further comprise heart rate variability, namely the difference between time intervals of two successive hear beats (generally useful for its variation based on stress or tiredness).

Figure 2:
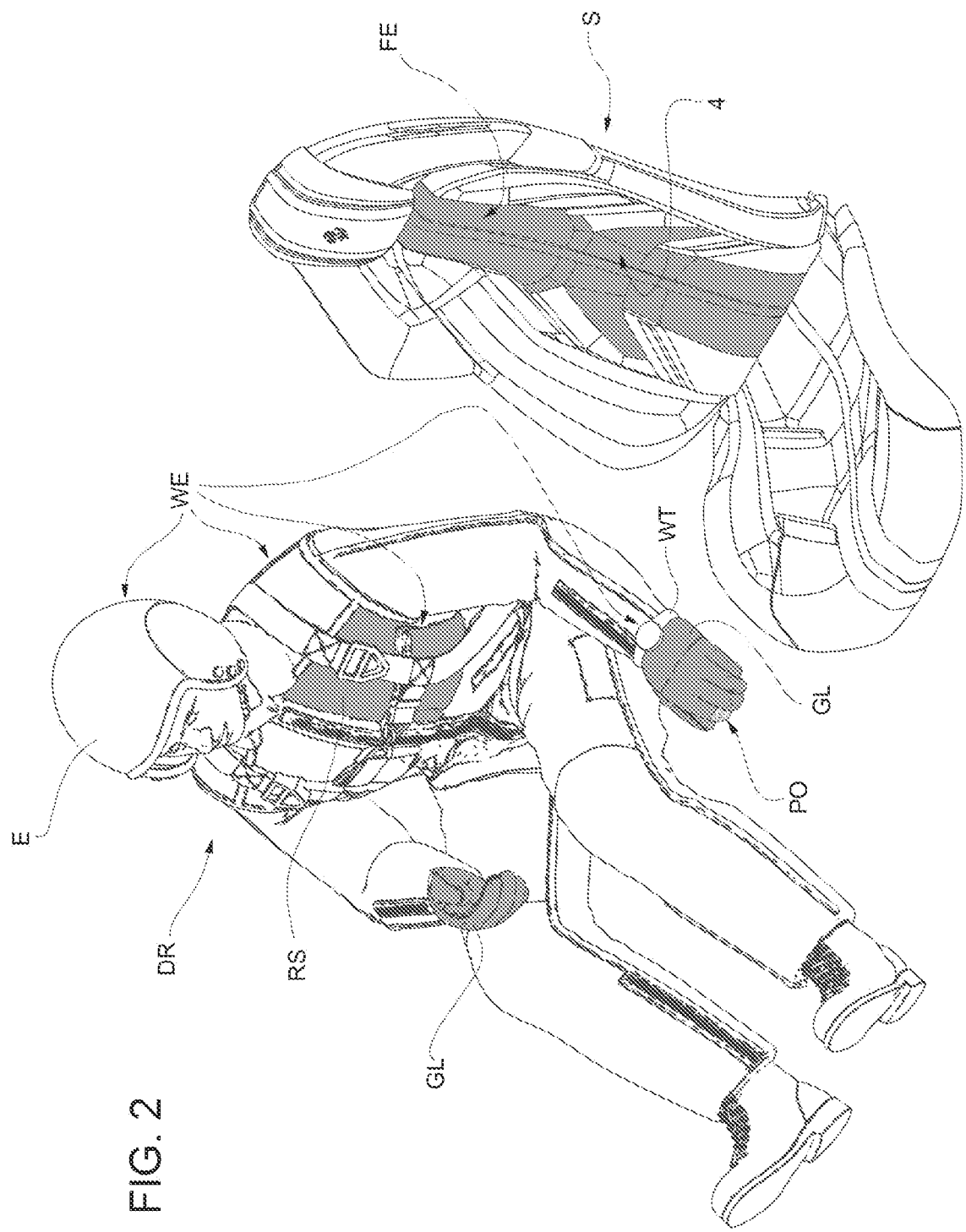
FIG. 2 is a second schematic perspective view of a portion o a vehicular system according to the invention.

In some preferred, non-limiting cases, such as the ones shown in FIGS. 1 and 2, the sensor devices 4 comprise one or more wearable elements WE, which can be worn by the driver DR (FIG. 2). In particular, for example in the non-limiting embodiment of FIGS. 1 and 2, the sensor devices 4 comprise a helmet E and/or a glove GL and/or a portion of a racing suite RS (or of an item of clothing underneath) and/or a smartwatch WT (in particular, a known smartwatch, which, therefore, will not be discussed in detail and is configured to detect HR, ECG, OS, etc.). Preferably, the glove GL comprises a pulse oximeter PO, in particular arranged in the area of a fingertip of the driver DR.

Advantageously, though not necessarily, at least one glove GL comprises a pressure sensor arranged in the area of the palm of the hand and/or of at least one finger.

Advantageously, though not necessarily, the sensor devices 4 comprise a GSR (Galvanic Skin Response) sensor configured to measure the electrical conductance of the skin (electrodermal response). In particular, the GSR sensor is configured to be arranged in the area of a wrist of the driver DR. More in particular, the sensor GSR is integrated in a glove GL. A strong emotion can cause stresses to the nervous system, with a consequent increase in the activity of sweat glands. In this case, the GSR sensor allows their activity PE to be monitored in the relation to the driver DR.

According to some preferred, though non-limiting embodiments, the glove GL is a biometric glove (in particular, of the type currently approved in the F1 championship). In this way, biometric gloves GL currently used for sole safety purposes (to monitor the vital parameters of a driver in case of a crash) are differently exploited to improve the driving experience (comfort and performances) of the driver DR.

Advantageously, though not necessarily, the racing suite RS comprises at least one item of clothing (in particular, covering the chest) provided with a temperature sensor and/or with a piezoelectric sensor and/or with electrodes (for a locally installed or remote electrocardiograph) and/or with a heart rate monitor.

Alternatively or in addition, the sensor devices 4 comprise one or more fixed elements FE (FIG. 2) installed in the area of a seat S configured to accommodate the driver DR or in the area o the steering wheel SW or of other components integral to the vehicle 2 (for example, wireless sensors, such as distance temperature sensors).

Advantageously, though not necessarily, the steering wheel SW comprises (in case it is not integrated in the glove GL) a conductive sensor to process an electrocardiogram ECG (detecting, at the same time, the heart rate HR). In particular the steering wheel SW, if it is not integrated in the glove GL, comprises a photoplethysmogram (PPG sensor) to detect changes in the blood volume of the driver DR.

Advantageously, though not necessarily, the sensor devices 4 comprise, among the fixed elements FE, a radar sensor arranged, in particular, in the area of the seat S, preferably behind the back of the driver DR.

Figure 4:
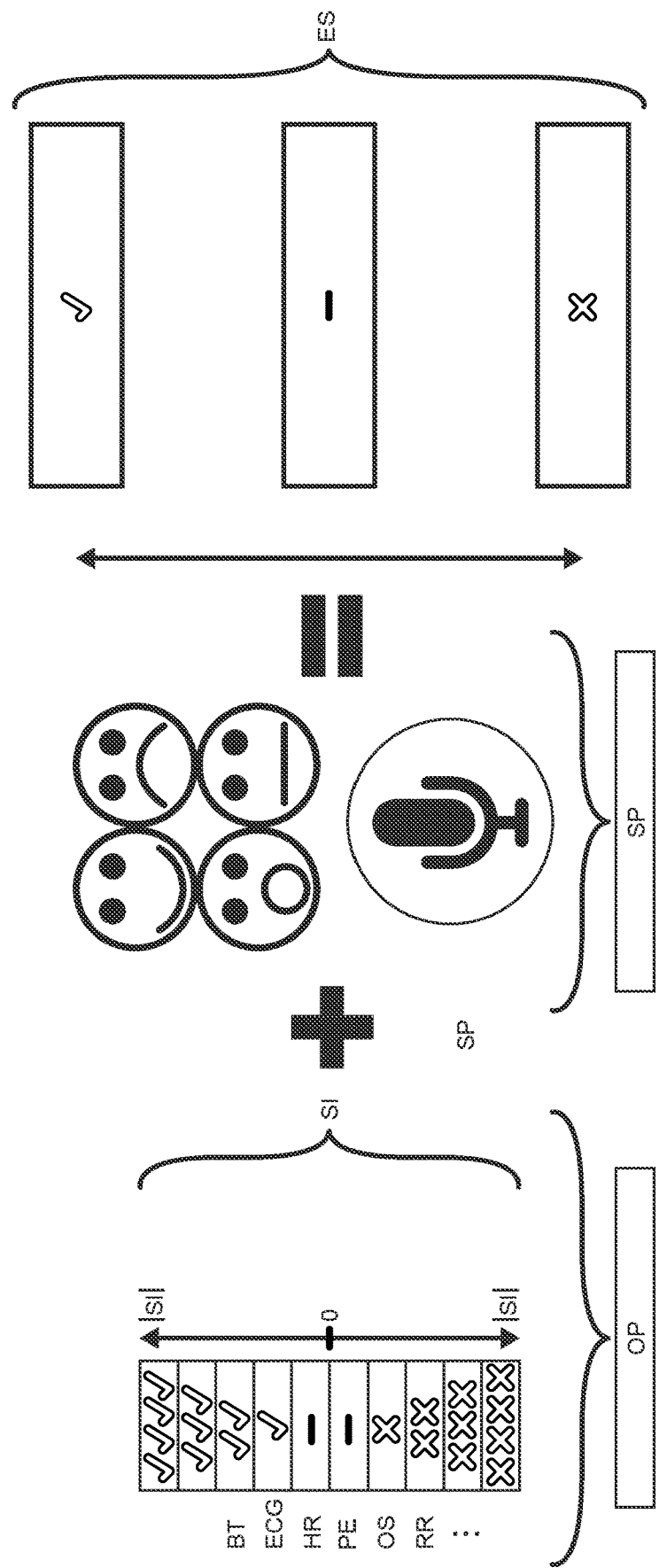
FIG. 4 is a possible schematic diagram for the processing of a psychophysical state according to a method according to the invention.

Furthermore, the vehicular system 1 comprises one or more sensor devices 5 configured to detect, in use, one or more subjective parameters SP of the driver DR. The term "subjective parameters" indicates those parameters that characterize a person differently from others and that change based on the psychophysical state of the driver (therefore, characterizing biometric parameters, such as fingerprints, have to be excluded). In particular, the subjective parameters SP are facial expressions FEX and vocal expressions VEX (FIGS. 4 and 5). As a matter of fact, these parameters characterize a driver DR from another and, at the same time, change depending on his/her psychophysical state. Preferably, therefore, the subjective parameters SP.

Advantageously, though not necessarily, the sensor devices 5 comprise at least one microphone M configured to detect vocal expressions VEX of the driver DR and/or an optical sensor 7, in particular a camera and/or thermal camera C, configured to detect facial expressions FEX of the driver DR. In particular, the camera C and the microphone M are configured to detect facial expressions FEX (sadness, crying, eyelid opening/closing frequency, smile, laughter, etc.) and vocal expressions VEX (tone of voice, elation, etc.) based on known face-tracking/face-analysis and voice-tracking/voice-analysis algorithms, respectively, which, hence, are not described in detail herein.

In addition, the vehicular system 1 comprises a processing unit 6 connected to the devices 4 and 5 and configured to process (namely, numerically calculate) the value of a vital state index SI as a function of said one or more objective vital parameters OP detected and to process (namely, determine), starting from the objective vital parameters OP and as a function of the subjective parameters SP, the psychophysical state ES of the driver DR. In detail, the processing unit 6 is also configured to execute the algorithms mentioned above.

According to a further non-limiting embodiment of the invention, there is provided a method of processing the psychophysical state of a driver DR to improve the driving experience of a road vehicle 2 driven by a driver DR, in particular when driving on a track T.

The method comprises the step of cyclically detecting (while driving) one or more objective vital parameters OP of the driver DR by means of the sensors 4 described above and installed within the vehicular system 1 (in other words, both the fixed elements FE and the wearable elements WE).

The method further comprises the step of processing (through the processing unit 6) the value of a vital state index SI as a function of the objective vital parameters OP detected.

According to a preferred, though non-limiting embodiment, the value of the vital state index SI is an absolute value or an average (in particular, a weighted average). In particular, since the objective vital parameters OP change at very different intervals, the method entails applying a relative correction weight $\alpha$, $\beta$, $\gamma$, $\delta$ to each objective vital parameter OP so as to standardize them on one single comparable scale. In detail, the value of the vital state index SI indicates to what extent the current objective vital parameters OP are far from neutral reference parameters. In other words, the value of the vital state index SI is a measure of the difference between the measured objective vital parameters OP and objective vital parameters OP considered as reference (under substantially neutral psychophysical conditions).

Advantageously, though not necessarily, the method further comprises a tuning step, which is prior to the (aforesaid) cyclic steps described herein and during which the objective vital parameters OP of the driver are recorded in a rest (neutral) condition, in particular when the vehicle 2 is parked. In particular, the objective vital parameters OP detected during the tuning step are used as reference in the calculation of the vital state index SI. More precisely, the calculation of the vital state index SI uses the difference between the objective vital parameters OP detected during the tuning step and the objective vital parameters OP cyclically detected while driving.

According to a non-limiting embodiment, by way of (simplified) example and only using, as parameters OP, hear rate HR, respiratory rate RR, body temperature BT and oxygen saturation OS, the value of the index SI is calculated as the (weighted) average of the difference between each reference parameter OP and the relative measured parameter OP (cyclically detected while driving), all divided by the respective reference parameter so as to quantify, in percentage, the difference between the reference parameters OP and the measured parameters OP. In particular, according to this example, the value of the index SI is measured according to the following formula:

$$|SI| = \text{mean}\left\{\alpha\frac{(HR_N - HR_M)}{HR_N}; \beta\frac{(RR_N - RR_M)}{RR_N}; \gamma\frac{(BT_N - BT_M)}{BT_N}; \delta\frac{(OS_N - OS_M)}{OS_N}\right\}$$

wherein $\alpha$, $\beta$, $\gamma$ and $\delta$ are respective weights (for example, calculated in an empiric manner or by means of reference tables); wherein subscript N indicates the reference parameter OP (in a neutral psychophysical condition of the driver DR, for example recorded during the tuning step) and subscript M indicates the measured parameter OP. Obviously, this formula can be re-adjusted so as to comprise all the parameters OP described above, in order to consider their difference from reference values.

The value of the index SI obtained by so doing provides the processing unit 6 with the fraction of difference between the reference parameters OP and the measured ones. This leads to empirically or theoretically determining threshold values beyond which the vehicular system 1 carries out actions protecting the driver DR and his/her comfort or gives inputs to improve his/her performance (if, in certain areas, an excessive stress or a lack of preparation is detected). However, there are conditions in which the objective parameters are not sufficient to completely define the psychophysical state ES of the driver DR. For example a high heart and respiratory rate, together with a heart arrhythmia, can be symptoms both of an anxiety/worry psychophysical state and of a surprise/joy psychophysical state. In other words, the sole objective parameters OP cannot define whether the psychophysical state ES of the driver is positive (leaning towards happiness, joy—indicated with ✓ in FIG. 4) or negative (leaning towards panic, anxiety, fear—indicated with X in FIG. 4). The greater the intensity of the difference between the reference parameters OP and the measured parameters OP, the greater the value of the vital state index SI.

Therefore, in addition, the method comprises the step of cyclically detecting (while driving) one or more subjective (psychophysical) parameters of the driver DR by means of the sensors 5 installed within the vehicular system 1. Advantageously, though not necessarily, this step entails analysing the facial expressions FEX or the vocal expressions VEX of the driver so as to establish whether the psychophysical state of the driver DR is positive or negative.

According to some non-limiting embodiments, such as the one shown in FIG. 1, the subjective parameters SP of the driver DR are facial expressions FEX, in particular detected by means of the optical sensor 7.

Alternatively or in addition, as shown in the non-limiting embodiment of FIG. 1, the subjective parameters SP of the driver DR are vocal expressions VEX, in particular detected by means of a microphone.

According to some non-limiting embodiments, the method comprises a first sub-step of detecting the facial expressions FEX and a second sub-step, subordinate to the first one (namely, in case the first one does not manage to exactly understand an expression useful to determine the psychophysical state ES of the driver), of detecting the vocal expressions VEX, in particular by asking pre-set questions to the driver DR and by listening through the microphone M.

Preferably, the method comprises the further step of protecting the privacy of the driver DR using suitable encryption algorithms both of the objective parameters OP and of the subjective parameters SP.

In some preferred, though non limiting cases, the driver DR selects which objective parameters OP and/or which subjective parameters SP and/or which boundary factors to share with the vehicular system 1.

In particular, following the detections of the sensors 4 and 5 and the processing of the vital state index SI, the method entails processing, starting from the objective vital parameters OP and as a function of the subjective parameters SP, the psychophysical state ES of the driver.

According to some non-limiting embodiments, like the one shown in FIG. 5, the objective vital parameters OP are selected from the group consisting of: heart rate HR, electrocardiogram ECG, respiratory rate RR, sweat gland activity PE, body temperature BT, oxygen saturation OS, or any combination thereof.

Advantageously, though not necessarily and as schematically shown in the non-limiting embodiment of FIG. 4, the method entails maintaining or changing the sign of the value of the state index SI as a function of the subjective parameters SP detected by the sensor devices 5. In this way, the psychophysical state ES is defined based on the positive or negative sign.

Advantageously, though not necessarily, in order to improve the flexibility and the reliability of the vehicular system 1, the value of the vital state index SI (in particular, the reference values) is corrected (adding or subtracting a predefined correction factor) as a function of one or more boundary factors, in particular the profiling data of the driver, the height of the vehicle, anthropometric data or any combination thereof. In this way, for example, a more accurate analysis can be carried out differentiating normal or abnormal values of drivers with different profiles and features. In particular, according to some preferred non-limiting embodiments, the driver DR selects which boundary factors he/she wants to share with the vehicular system 1, autonomously selecting the degree of precision of the monitoring.

The term "anthropometric data" identifies all possible measures concerning the body of a driver DR, such as, for example, length and/or thickness of the limbs, height, position of body joints, etc.

According to some non-limiting embodiments, at least part of the aforesaid boundary factors are detected by interrogating the driver DR via an interface device 8. In other words, the processing unit 6 is configured to receive, based on the data received from the interface device 8, at least part of the boundary factors. In particular, the interface device 8 is configured to detect images and/or anthropometric data of the driver DR.

Figure 3:
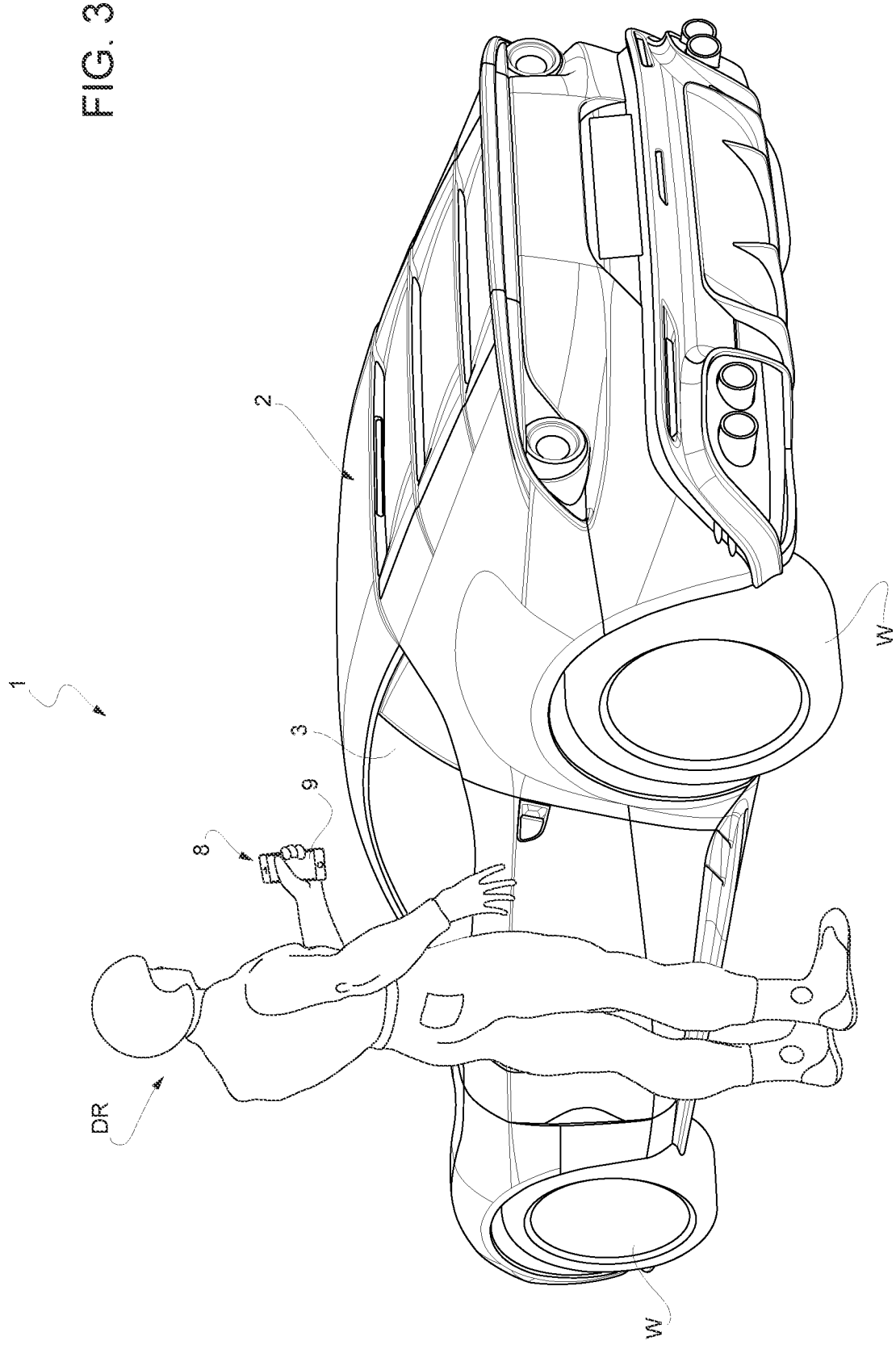
FIG. 3 is a view from the outside of a high-performance road vehicle, where a vehicular system according to the invention can be installed.

In some non-limiting cases and according to the non-limiting embodiment of FIG. 3, the interface device 8 is a smartphone 9. In other non-limiting cases, alternatively or in addition, the interface device is a pc, a tablet, a virtual assistant or a control panel on the inside of the vehicle 2.

Advantageously, though not necessarily, the method comprises the further step of estimating the driving ability of the driver DR as a function of the psychophysical state ES of the driver DR while driving on a track T.

In some non-limiting cases, the method comprises a further step of suggesting a dedicated training to the driver DR as a function of the (previously detected) psychophysical state ES and of the estimated driving ability. In particular, the driver DR receives information on his/her performance to be displayed on the interface device 8, for example specific training (both from a physical and from a mental point of view) to better tackle some parts of the track T.

In particular, the method comprises the further step of suggesting corrective actions CA to the driver DR during a lap of a track following the estimation of the driving ability, wherein the quality and/or quantity of the suggested corrective actions CA is filtered according to the estimated driving ability.

Advantageously, though not necessarily, the vehicular system 1 is configured to carry out the method disclosed so far.

Even though the invention described above relates to a specific embodiment example, it should not be considered as limited to said embodiment example, for its scope of protection also includes all those variants, changes or simplifications covered by the appended claims, such as, for instance, a different method for detecting the parameters SP and OP of the driver DR, a different type of vehicle (for example, a two-wheel vehicle or a front-drive vehicle), different parameters OP and SP, a different method for calculating the index SI, etc.

The invention offers many advantages.

First of all, the method and the vehicular system described herein allow users not only to understand the state of the vehicle, but also to monitor the psychophysical state of the driver, improving his/her driving experience, especially on a track, by suggesting corrective actions.

Furthermore, in case of less experienced drivers, dedicated training suggestion can be made, also aimed at improving the physical condition of the driver.

A further advantage of this invention lies in the possibility of warning the driver in case the measured parameters OP are excessively different from the reference parameters OP, exceeding a predefined threshold value, which delimits the normality range of the parameters.

Furthermore, the invention permits a real-time analysis of the driver's parameters OP and SP, in order to identify the reactions of the driver and benefit therefrom in terms of psychophysical preparation and management protocols, so as to provide suggestions and/or corrective actions matching his/her driving abilities.

In addition, for the preparation of professional drivers, this method could also be used in a simulator, so as to best train the driver even before getting on the track.

LIST OF THE REFERENCE NUMBERS OF THE FIGURES 1 vehicular system
2 vehicle
3 passenger compartment
4 sensor device
5 sensor device
6 processing unit
7 optical sensor
8 interface device
9 smartphone
AD anthropometric data,
BC boundary factors
BT body temperature
C camera
CA corrective actions
DR driver
E helmet
ECG electrocardiogram
ES psychophysical state
FE fixed elements
FEX facial expressions
GL glove
HR heart rate
M microphone
OP objective vital parameters
OS oxygen saturation
PE sweat gland activity
PO pulse oximeter
RR respiratory rate
RS racing suit
S seat
SI vital state index
SP subjective parameters
SW steering wheel
T track
VEX vocal expressions
WE wearable elements
WT smartwatch

The invention claimed is:

1. A method of processing a psychophysical state of a driver (DR) to improve the driving experience of road vehicle (2) driven by the driver (DR); the method comprising:

recording one or more objective vital parameters (OP) of the driver (DR) while the road vehicle (2) is stationary to provide reference values for the one or more objective vital parameters (OP);

cyclically detecting one or more objective vital parameters (OP) of the driver (DR) during driving via one or more first sensors (4) installed within a vehicle system (1);

processing a value of a vital state index (SI), wherein the value of the vital status index (SI) is derived from a difference between the reference values for the one or more objective vital parameters (OP) when the vehicle is stationary and the detected one or more objective vital parameters (OP) of the driver (DR) during the driving;

cyclically detecting one or more subjective parameters (SP) of the driver (DR) by means of one or more second sensors (5) installed within the vehicle system (1) during the driving, wherein said one or more subjective parameters (SP) of the driver (DR) are facial expressions (FEX) and/or vocal expressions;

processing, starting with the value of the vital state index (SI) and according to the one or more subjective parameters (SP) during the driving, a psychophysical state of the driver (DR); and maintaining or changing a sign of the value of the state index (SI) to indicate a positive or negative psychophysical state depending on the one or more subjective parameters (SP).

2. The method according to claim 1, wherein the detected one or more objective vital parameters (OP) are selected from the group consisting of: heart rate (HR), electrocardiogram (ECG), respiratory rate (RR), sweat gland activity, body temperature (BT), oxygen saturation (OS), or any one of their combinations.

3. The method according to claim 1, wherein the value of the vital state index (SI) is processed by means of a weighted average of the detected one or more objective vital parameters (OP).

4. The method according to claim 1, wherein the vital state index value (SI) is corrected according to one or more boundary factors (BC); in particular comprising profiling data, altitude of the vehicle (2), anthropometric data, or any combination thereof.

5. The method according to claim 4, wherein at least part of the one or more boundary factors (BC) are detected by interrogating the driver (DR) via an interface device (8).

6. The method according to claim 1, wherein the facial expressions (FEX) are detected by means of an optical sensor (7) and/or the vocal expressions are detected by means of a microphone (M).

7. The method according to claim 1, further comprising protecting a privacy of the driver (DR) using appropriate encryption algorithms of both the one or more detected objective parameters (OP) and subjective parameters (SP); wherein the driver (DR) selects which of the one or more detected objective parameters (OP) and/or which subjective parameters (SP) and/or which boundary factors are to be shared with the vehicular system (1).

8. The method according to claim 1, further comprising estimating a driving ability as a function of the psychophysical state of the driver (DR) while driving along a track.

9. The method according to claim 8, further comprising a teaching step, during which the driver (DR) is suggested a dedicated training according to the psychophysical state and the estimated driving ability.

10. The method according to claim 8, further comprising suggesting corrective actions (CA) to the driver (DR) during a lap of a track following the estimation of the driving ability, wherein the quality and/or quantity of the suggested corrective actions (CA) is filtered according to the estimated driving ability.

11. A vehicular system (1) for enhancing the driving experience of a road vehicle (2) driven by a driver (DR); the vehicular system (1) comprising:
   one or more of first sensor devices configured to detect, in use, one or more objective vital parameters (OP) of the driver (DR);
   one or more of second sensor devices, configured to detect, in use, one or more subjective parameters (SP) of the driver (DR); and
   a processing unit (6), configured to process a value of a vital state index (SI) as a function of a difference between the one or more objective vital parameters (OP) detected during driving and at rest, to process, starting from the difference, and as a function of the one or more subjective parameters (SP), a psychophysical state of the driver (DR), and to maintain or change a sign of the value of the state index (SI) to indicate a positive or negative psychophysical state depending on the one or more subjective parameters (SP).

12. The vehicular system (1) according to claim 11, wherein the first sensor devices comprise one or more wearable elements (WE) comprising a helmet (E) and/or a glove and/or a portion of a suit.

13. The vehicular system according to claim 12, wherein the second sensor devices comprise at least one microphone (M) and/or one optical sensor (7) comprising a camera (C) or thermal camera (C).

14. The vehicular system according to claim 11, wherein the first sensor devices comprise one or more elements installed at a seat configured to accommodate a driver (DR).

* * * * *